(12) United States Patent
Kollgaard et al.

(10) Patent No.: US 9,797,867 B2
(45) Date of Patent: Oct. 24, 2017

(54) APPARATUS AND METHOD FOR INSPECTING A LAMINATED STRUCTURE

(71) Applicant: THE BOEING COMPANY, Chicago, IL (US)

(72) Inventors: Jeffrey R. Kollgaard, Seatle, WA (US); William J. Tapia, Graham, WA (US)

(73) Assignee: THE BOEING COMPANY, Chicago, IL (US)

( * ) Notice: Subject to any disclaimer, the term of this patent is extended or adjusted under 35 U.S.C. 154(b) by 1227 days.

(21) Appl. No.: 13/864,044

(22) Filed: Apr. 16, 2013

(65) Prior Publication Data
US 2013/0220018 A1 Aug. 29, 2013

Related U.S. Application Data

(63) Continuation-in-part of application No. 12/849,972, filed on Aug. 4, 2010, now Pat. No. 8,914,244.

(51) Int. Cl.
*G01B 5/28* (2006.01)
*G01N 29/04* (2006.01)
*G01N 29/06* (2006.01)

(52) U.S. Cl.
CPC .......... *G01N 29/04* (2013.01); *G01N 29/043* (2013.01); *G01N 29/0645* (2013.01); *G01N 2291/0231* (2013.01); *G01N 2291/044* (2013.01); *G01N 2291/0425* (2013.01); *G01N 2291/2636* (2013.01); *G01N 2291/2694* (2013.01)

(58) Field of Classification Search
CPC ... G01N 2291/0231; G01N 2291/2694; G01N 29/225; G01N 29/24; G01N 29/265; G01N 29/04

USPC .......................................................... 702/39
See application file for complete search history.

(56) References Cited

U.S. PATENT DOCUMENTS

| 4,413,517 A | 11/1983 | Soden |
| 4,510,812 A | 4/1985 | Feng |
| 5,094,108 A | 3/1992 | Kim |
| 5,596,989 A | 1/1997 | Morita |

(Continued)

FOREIGN PATENT DOCUMENTS

| CN | 201177617 Y | 1/2009 |
| GB | 1171377 A | 11/1969 |

(Continued)

OTHER PUBLICATIONS

UK IPO Search Report for GB1112980.6 dated Nov. 2, 2011.

(Continued)

*Primary Examiner* — Toan Le
*Assistant Examiner* — Xiuquin Sun
(74) *Attorney, Agent, or Firm* — Duft Bornsen & Fettig LLP (57) ABSTRACT

Systems and methods for inspecting a hole in a laminated structure. An exemplary system includes a transducer assembly configured to direct sound waves substantially parallel to a surface of the hole. The system further includes a controller that collects A-scan data for multiple rotational positions of the transducer assembly as the transducer assembly is rotated within the hole. The controller processes the A-scan data for the multiple rotational positions of the transducer assembly to generate B-scan data, and displays the B-scan data.

19 Claims, 8 Drawing Sheets

(56) References Cited

U.S. PATENT DOCUMENTS

| | | | | |
|---|---|---|---|---|
| 5,681,995 | A | * | 10/1997 | Ooura .................... G01N 29/11 376/249 |
| 5,921,931 | A | * | 7/1999 | O'Donnell ............... A61B 8/06 382/162 |
| 6,386,036 | B1 | | 5/2002 | Borza |
| 6,409,673 | B2 | * | 6/2002 | Yock ........................ A61B 8/12 600/463 |
| 7,222,514 | B2 | | 5/2007 | Kollgaard et al. |
| 2003/0089171 | A1 | * | 5/2003 | Kenefick ................ G01N 19/08 73/597 |
| 2005/0199065 | A1 | | 9/2005 | Dunegan |
| 2006/0213273 | A1 | * | 9/2006 | Lasser .................... G01N 29/07 73/606 |
| 2006/0265175 | A1 | | 11/2006 | Shimohamadi |
| 2007/0051177 | A1 | | 3/2007 | Kollgaard |
| 2007/0167821 | A1 | * | 7/2007 | Lee .......................... A61B 8/12 600/463 |
| 2008/0283332 | A1 | | 11/2008 | Ihn |
| 2009/0260442 | A1 | * | 10/2009 | Hara ....................... G01B 17/02 73/627 |

FOREIGN PATENT DOCUMENTS

| | | |
|---|---|---|
| JP | 57158550 A | 9/1982 |
| WO | 2008157427 A1 | 12/2008 |
| WO | 2009/152143 A1 | 12/2009 |

OTHER PUBLICATIONS

NDT Resource center website, http://www.ndt-ed.org/educationresources/communitycollege/ultrasonics/cc_ut_index.htm, Apr. 14, 2010. Section on Angle Beam I.

Langenberg, K.J., et al., "On the Nature of the So-Called Subsurface Longitudinal Wave and/or the Surface Longitudinal "Creeping" Wave," Res Nondestr Eval (1990) 2:59-81, Springer-Verlag, New York.

Pilarski, A., et al., "Utility of Subsurface Longitudinal Waves in Composite Material Characterization," vol. 27, Jul. 1989, pp. 226-233.

* cited by examiner

APPARATUS AND METHOD FOR INSPECTING A LAMINATED STRUCTURE

RELATED APPLICATIONS

The patent application is a continuation-in-part of co-pending U.S. non-provisional patent application Ser. No. 12/849,972, filed on Aug. 4, 2010 and identically entitled, which is hereby incorporated by reference.

FIELD

This disclosure relates generally to the inspection of structures, and more particularly to assessing the condition of a laminated structure.

BACKGROUND

Lightweight composite materials are being used more extensively in the aerospace industry for both commercial and military aircraft and other aerospace vehicles, as well as in other industries. The structures using these composite materials may be formed using multiple plies or layers of material that are laminated together to form a high-strength structure. These structures may undergo further machining processes during manufacturing and assembly of vehicles (e.g., drilling, cutting, countersinking, shimming, fastener removal, etc.), may undergo flight and ground operations (e.g., maintenance, repair, retrofit, or overhaul), and may suffer damage from impact or other causes. Therefore, manufacturing or maintenance crews may need to inspect the condition of the laminated structure.

SUMMARY

Embodiments described herein provide a new way of inspecting holes in laminated structures using ultrasonic testing. An inspection device as described herein includes a transducer assembly for generating ultrasonic sound waves and detecting echo waves from reflecting surfaces proximate to a hole in a laminated structure. When the transducer assembly is inserted in the hole of the laminated structure, the transducer assembly is able to direct sounds waves substantially parallel to the surface of the hole. Thus, the sound waves will propagate through the layers of the laminated structure at a shallow depth parallel to the direction of the hole, and will be reflected by anomalies in the layers of the laminated structure, such as a delaminated area. The transducer detects echo waves that are reflected by anomalies in the layers of the laminated structure. This has the advantage of being able to identify damage in layers behind the first delaminated layer. Because the transducer assembly is able to direct sound waves that propagate so close to the surface of the hole, the transducer assembly can be used to effectively inspect the condition of the hole in the laminated structure from inside the hole and behind any delaminations detected with normal pulse-echo ultrasonics. This allows for a complete characterization of damage in the hole, whereas conventional ultrasonic techniques only identify the shallowest damage in a hole.

According to the embodiments described herein, the transducer assembly is rotated in the hole of the laminated structure to inspect the condition of the hole around its circumference. When an ultrasonic measurement is taken, the measurement data is associated with the rotational position of the transducer assembly. Thus, as the transducer assembly is rotated, measurement data is collected for multiple rotational positions of the transducer assembly. Taking advantage of the width of the sound beam generated by the transducer assembly, this measurement data can then be plotted in a B-scan presentation to show any anomalies found in the layers of the laminated structure proximate to the hole.

One embodiment comprises a method of inspecting a hole in a laminated structure with an ultrasonic inspection device. The method includes inserting the transducer assembly of the ultrasonic inspection device in the hole of the laminated structure. The method further includes collecting A-scan data for multiple rotational positions of the transducer assembly as the transducer assembly is rotated within the hole. The method further includes processing the A-scan data for the multiple rotational positions of the transducer assembly to generate B-scan data, and displaying the B-scan data. For instance, the B-scan data may be displayed in terms of depth in the hole versus rotational position of the transducer assembly.

Another embodiment comprises an ultrasonic inspection device for inspecting a hole in a laminated structure. The ultrasonic inspection device includes a transducer assembly configured to direct sound waves substantially parallel to the surface of the hole. The ultrasonic inspection device further includes a controller configured to collect A-scan data for multiple rotational positions of the transducer assembly as the transducer assembly is rotated within the hole, to process the A-scan data for the multiple rotational positions of the transducer assembly to generate B-scan data, and to display the B-scan data.

Another embodiment comprises a method of inspecting a hole in a laminated structure. The method includes inserting a transducer assembly of an ultrasonic probe into the hole in the laminated structure. The method further includes collecting A-scan data for multiple rotational positions of the transducer assembly as the transducer assembly is rotated within the hole. The A-scan data is collected by determining a present rotational position of the transducer assembly, generating a sound wave in a transducer of the transducer assembly that is directed toward a side of an elongated transducer rod, wherein the sound wave refracts when passing through the side of the transducer rod at an angle substantially parallel to a surface of the hole. The method further includes receiving an echo wave(s) at the transducer, and converting the echo wave(s) into A-scan data that is associated with the present rotational position of the transducer assembly. The method further includes processing the A-scan data for the multiple rotational positions of the transducer assembly to generate B-scan data, and displaying the B-scan data.

The features, functions, and advantages that have been discussed can be achieved independently in various embodiments or may be combined in yet other embodiments further details of which can be seen with reference to the following description and drawings.

DESCRIPTION OF THE DRAWINGS

Some embodiments are now described, by way of example only, and with reference to the accompanying drawings. The same reference number represents the same element or the same type of element on all drawings.

DESCRIPTION

The figures and the following description illustrate specific exemplary embodiments. It will thus be appreciated that those skilled in the art will be able to devise various arrangements that, although not explicitly described or shown herein, embody the principles described herein and are included within the contemplated scope of the claims that follow this description. Furthermore, any examples described herein are intended to aid in understanding the principles of the disclosure, and are to be construed as being without limitation. As a result, this disclosure is not limited to the specific embodiments or examples described below, but by the claims and their equivalents.

Figure 1:
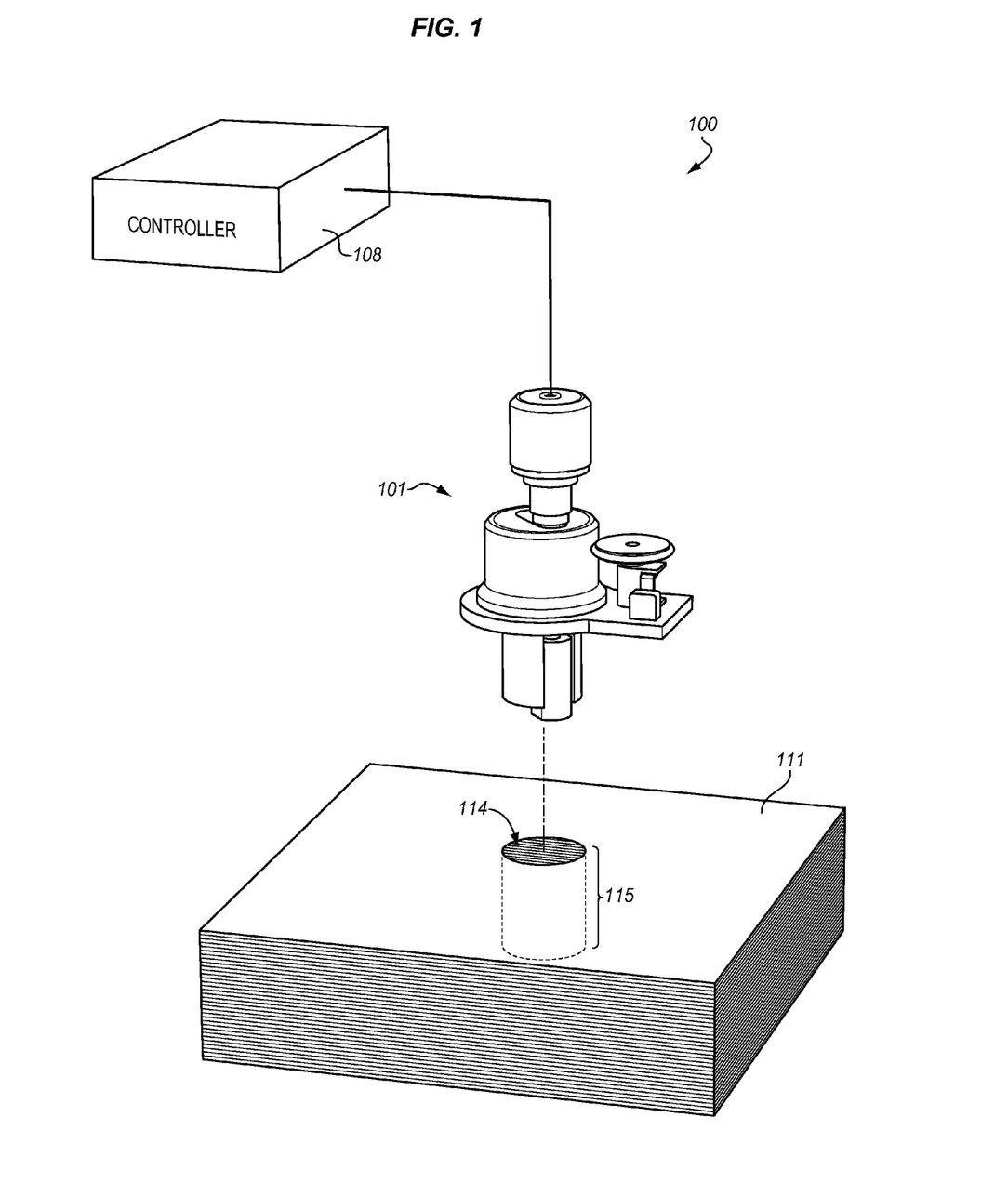
FIG. 1 illustrates an ultrasonic inspection device for a laminated structure in an exemplary embodiment.

FIG. 1 illustrates an ultrasonic inspection device 100 for a laminated structure 111 in an exemplary embodiment. Laminated structure 111 comprises multiple layers of material that are sandwiched to form a composite. Laminated structure 111 has a variety of applications, such as a part on an aircraft. Inspection device 100 is able to detect imperfections or anomalies proximate to a hole 114 in laminated structure 111. Hole 114 as defined herein is any opening, gap, or aperture in laminated structure 111. For example, hole 114 may represent a bolt hole in laminated structure 111. Hole 114 has a surface 115 around its circumference that may become damaged. Therefore, inspection device 100 is able to inspect the condition of hole 114.

Inspection device 100 includes a controller 108 coupled to an ultrasonic probe 101. Controller 108 comprises any device that generates and processes signals for ultrasonic measurements. Controller 108 may include a power supply, a pulse generator/receiver, a computer interface, hardware and/or software, instrument control, and signal processing. Ultrasonic probe 101 is configured to be inserted within hole 114 of laminated structure 111, and to generate ultrasonic sound waves that propagate substantially parallel to surface 115 of hole 114. For example, the ultrasonic sound waves will propagate upward or downward substantially parallel to the surface 115 of hole at a shallow depth.

Figure 2:
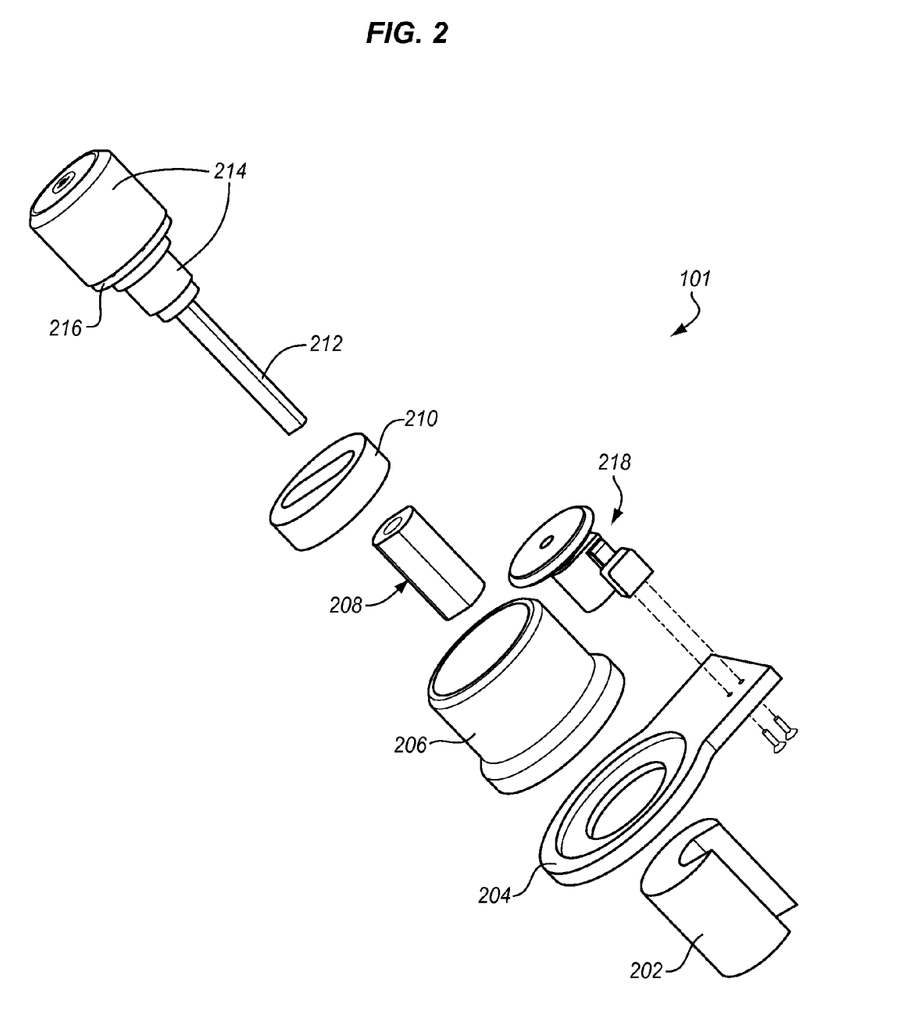
FIG. 2 is an exploded view of an ultrasonic probe in an exemplary embodiment.

FIG. 2 is an exploded view of ultrasonic probe 101 in an exemplary embodiment. The structure shown in FIG. 2 is one example, as ultrasonic probe 101 may have many different configurations. Ultrasonic probe 101 includes a hole insert 202 and a universal bell housing 206 moveably coupled to positioning member 204. Hole insert 202 is the portion of ultrasonic probe 101 that is inserted into hole 114. Thus, hole insert 202 has a diameter that corresponds to the diameter of hole 114 (see FIG. 1) so that it may be inserted into hole 114. Positioning member 204 sits on an outer surface of laminated structure 111 when hole insert 202 is inserted in hole 114. Bell housing 206 connects to an opposing side of positioning member 204. Bell housing 206 and hole insert 202 are able to rotate in relation to position member 204.

Ultrasonic probe 101 further includes a transducer assembly 208. Although not visible in FIG. 2, transducer assembly 208 includes at least one transducer and a transducer rod. A transducer comprises a piezoelectric element configured to generate ultrasonic longitudinal sound waves (also referred to as L-waves), and to detect reflections of the sound waves. A transducer rod is an elongated member that is used to direct sound waves emitted by the transducer substantially parallel to the surface 115 of hole 114. Transducer assembly 208 fits within the slot in hole insert 202. Thus, when hole insert 202 is rotated within the hole 114 of laminated structure 111, transducer assembly 208 will likewise rotate within hole 114 and sweep a path around the interior of hole 114.

Ultrasonic probe 101 further includes a mechanism for controlling the depth of transducer assembly 208. The depth mechanism includes a slotted spacer 210 and a threaded shaft 212 that connects to transducer assembly 208. The depth mechanism further includes a lock mechanism 214 and a depth index wheel 216. When depth index wheel 216 is turned on threaded shaft 212, this controls the depth of transducer assembly 208 within hole 114. Lock mechanism 214 is loosened when the depth of transducer assembly 208 is adjusted with depth index wheel 216, and is tightened to fix the depth of transducer assembly 208.

Ultrasonic probe 101 further includes a rotary encoder 218 that is in contact with universal bell housing 206 or some other part of ultrasonic probe 101. Rotary encoder 218 is able to monitor the rotational position of transducer assembly 208, and provide position data to controller 108 (see FIG. 1). Although not shown in FIG. 2, ultrasonic probe 101 may further include an actuator to impart rotational movement on transducer assembly 208. The actuator would turn transducer assembly 208 in response to a control signal from controller 108 (see FIG. 1).

Figure 3:
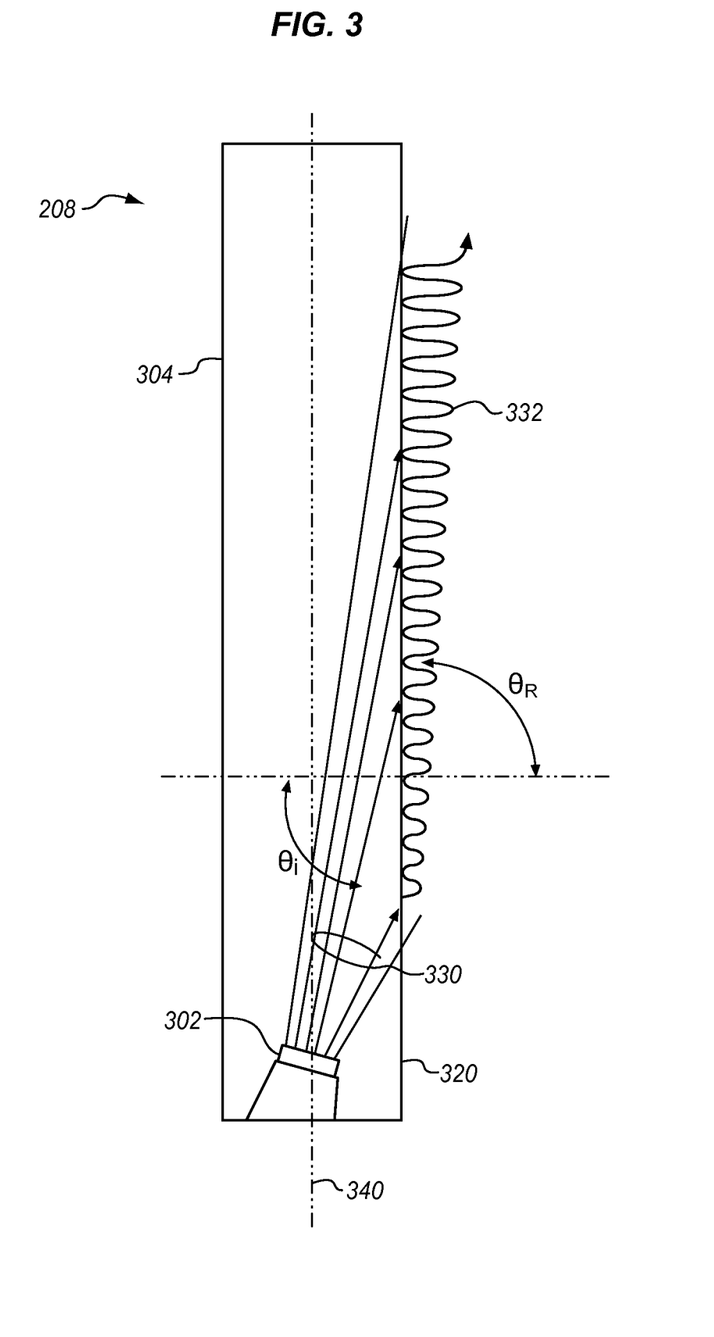
FIG. 3 is a cross-sectional view of a transducer assembly in an exemplary embodiment.

FIG. 3 is a cross-sectional view of transducer assembly 208 in an exemplary embodiment. Transducer assembly 208 includes a transducer 302 and a transducer rod 304. Transducer 302 is coupled to an end of transducer rod 304 and angled toward a side 320 of transducer rod 304 to direct sound waves toward the side of transducer rod 304. Assume for example that transducer 302 generates a sound wave or pulse. The sound wave (shown as reference number 330) is directed toward the side 320 of transducer rod 304 at an angle referred to as an angle of incidence $\theta_i$. The sound wave 330 emitted by transducer 302 is shown as a multiple arrows that are directed toward the side 320 of transducer rod 304 to illustrate that the sound waves for a beam of a finite width spread slightly as they are emitted from transducer 302. The spread of the sound waves from a circular element may be calculated by the half angle formula:

$\sin \theta = 1.2(V/DF)$, where $V$=material velocity,
$D$=diameter of the transducer element, and
$F$=frequency.

In the case of a rectangular or elongated transducer 302, the formula is modified. A more appropriate term for the transducer dimension that is responsible for the sound beam width in transducer rod 304 is transducer length. The spread of the sound waves from transducer 302 may be calculated by:

$\sin \theta = 1.2(V/LF)$, where $V$=material velocity,
$L$=length of the transducer element, and
$F$=frequency.

As the sound wave passes through the side 320 of transducer rod 304, the sound wave is refracted (by the material of transducer rod 304) at an angle of refraction $\theta_R$. The sound wave refracted through the side of transducer rod 304 is shown as reference number 332. Due to the angle of incidence $\theta_i$ and the material used for transducer rod 304, the angle of refraction $\theta_R$ is near 90 degrees. Therefore, the sound wave is launched out of transducer rod 304 and propagates substantially parallel to the longitudinal axis 340 of transducer rod 304.

Transducer assembly 208 may have many different configurations to cause the sound wave to propagate parallel to the surface of hole 114. In one example of a different configuration, a transducer may be mounted on one end of transducer rod 304, and the other end of transducer rod 304 may have a reflective surface that reflects a sound wave toward the side of transducer rod 304. The reflective surface may have a single flat face, multiple facetted angles, a curved surface, a conical surface, a parabolic surface, etc.

Figure 4:
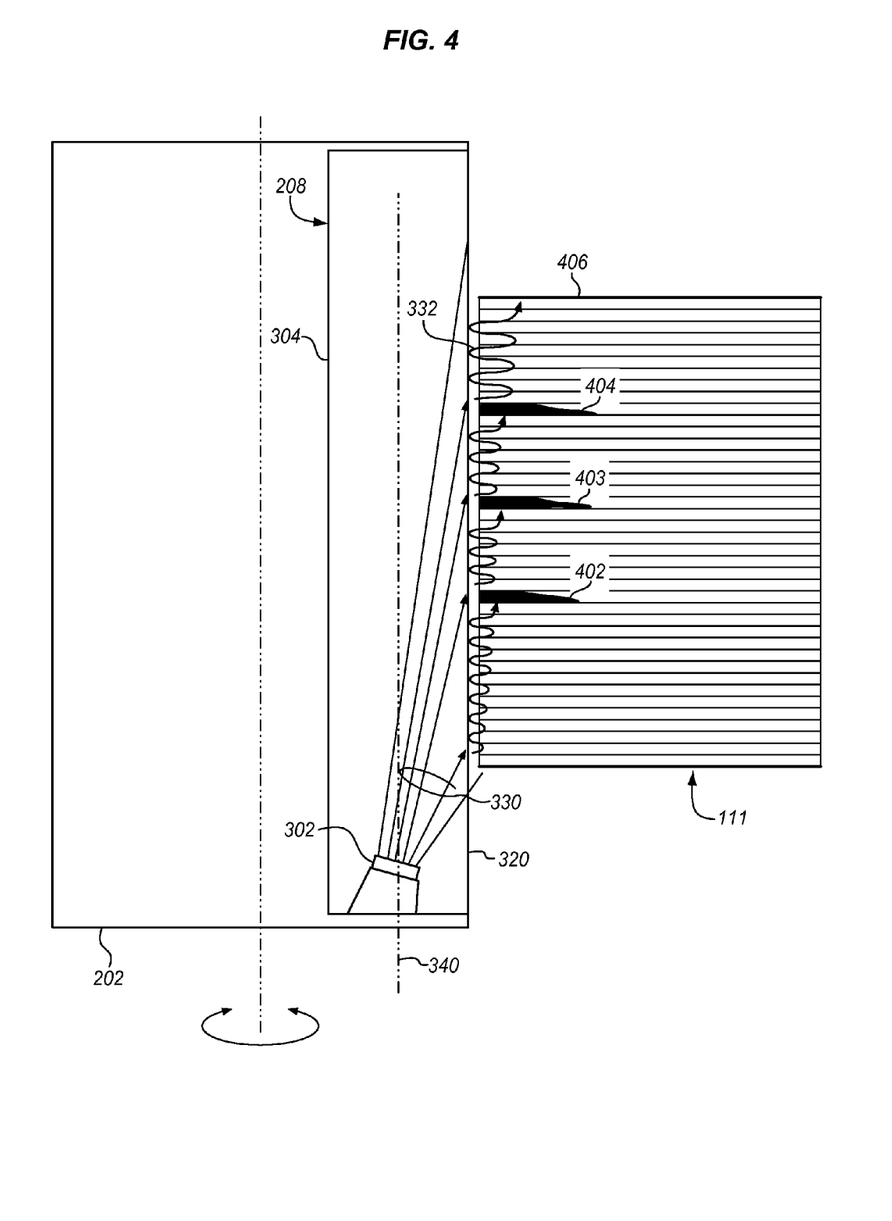
FIG. 4 is a cross-sectional view of a transducer assembly inserted into a hole in a laminated structure in an exemplary embodiment.

Because transducer rod 304 is able to refract sounds waves substantially parallel to the surface of hole 115, ultrasonic probe 101 can be used to inspect the condition of hole 114 in laminated structure 111. FIG. 4 is a cross-sectional view of transducer assembly 208 inserted into hole 114 in laminated structure 111 in an exemplary embodiment. FIG. 4 also shows anomalies 402-404 in laminated structure 111 where layers have become disbonded or delaminated from one another. As the refracted sound wave (referred to as an ultrasonic subsurface longitudinal wave (SSL-wave)) propagates through laminated structure 111 at a shallow depth, the sound wave may be reflected by surfaces within structure 111. The reflecting surfaces within laminated structure 111 may be "normal" to laminated structure 111, such as an outer surface or a joint. However, other reflecting surfaces may be the result of damage, delamination, etc., within the layers of structure 111 proximate to hole 114. In FIG. 4, as the sound wave from transducer assembly 208 propagates through laminated structure 111, the anomalies 402-404 will reflect the sound wave. Each anomaly 402-404 will reflect 100% of the impinging sound wave. However, due to the width of the sound wave, individual reflections from sequential anomalies are possible. By deliberately engineering transducer 302 to produce a sound wave (or beam) of a maximum width, a larger span of material can be covered. The outer surface 406 of laminated structure 111 will also reflect the sound wave. The sound waves that are reflected (referred to herein as reflected waves or echo waves) propagate back through transducer rod 304 toward transducer 302 on substantially the same path as the original sound wave. Those skilled in the art of pulse echo ultrasonic inspection are aware that certain transducers can both transmit and receive ultrasonic signals. Transducer 302 converts the echo waves into an electrical signal, and provides the electrical signal back to controller 108 (see FIG. 1). Controller 108 can then process the electrical signal received from transducer 302 to detect imperfections in laminated structure 111. Controller 108 is able to differentiate the echo waves associated with an anomaly in laminated structure 111 from the echo waves in the normal regions of laminated structure 111 with signal processing.

Figure 5:
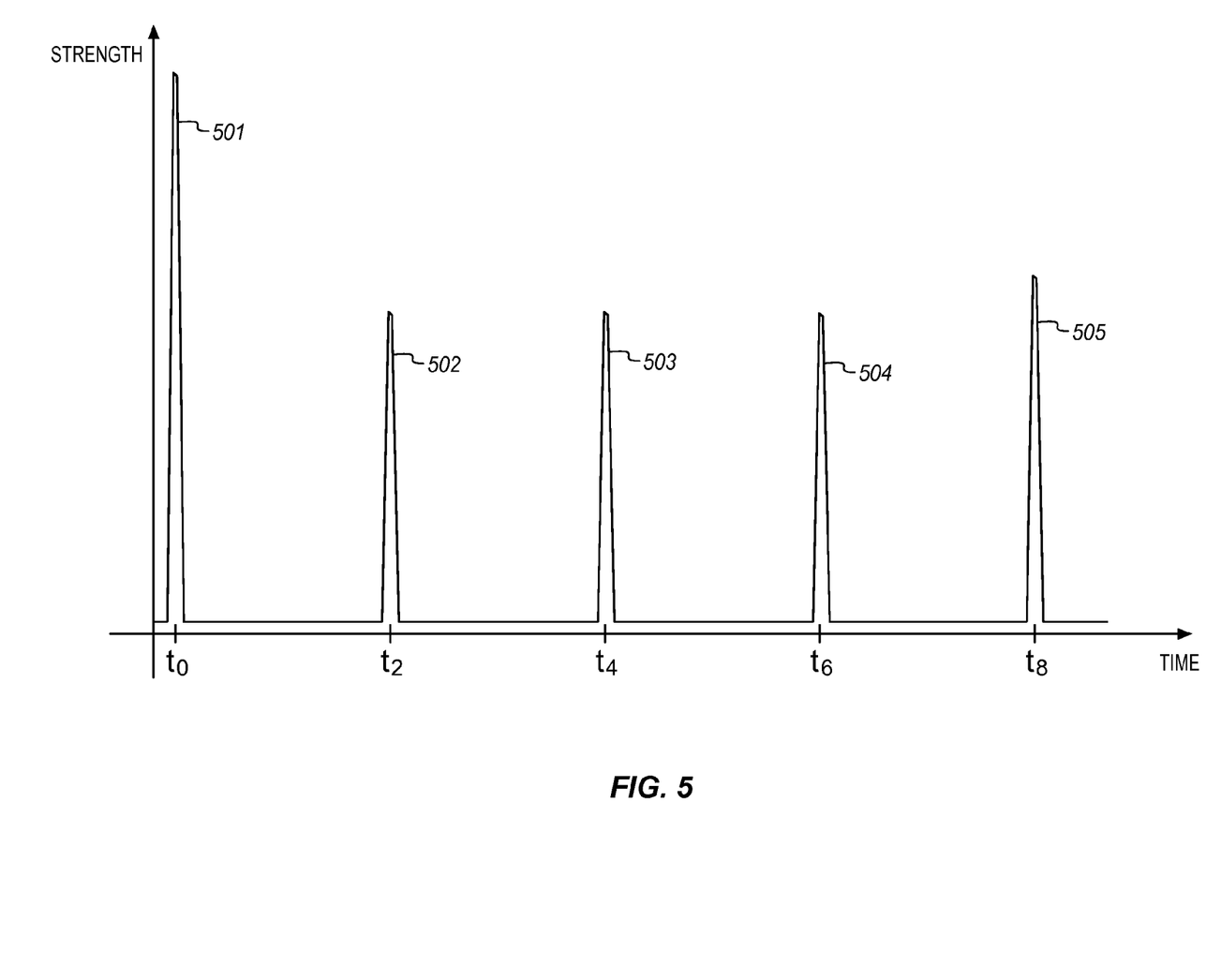
FIG. 5 is a graph illustrating A-scan data for an ultrasonic measurement in an exemplary embodiment.

One way of displaying raw ultrasonic data is referred to as an "A-scan". An A-scan presentation displays the amount of ultrasonic energy received as a function of time. FIG. 5 is a graph illustrating A-scan data in an exemplary embodiment. The vertical axis in the graph in FIG. 5 represents signal strength, while the horizontal axis represents time. The first pulse 501 in FIG. 5 represents the initial pulse (or sound wave) generated by transducer 302, which is near time t0. The second pulse 502 represents the echo wave from anomaly 402 received at time t2, the third pulse 503 represents the echo wave from anomaly 403 received at time t4, and the fourth pulse 504 represents the echo wave from anomaly 404 received at time t6. The fifth pulse 505 represents the echo wave from outer surface 406 received at time t8. This type of A-scan data is possible because the crystal of transducer 302 is shaped such that a maximum beam width is achieved. If the width of the sound wave from transducer 302 were narrow, the first anomaly 402 in the sound path would block the sound from reaching the other anomalies 403 and 404. However, because the sound wave is given a maximum width in the embodiments described herein, simultaneous presentation of anomalies at different depths is possible.

Another way of displaying ultrasonic data is referred to as a "B-scan". A B-scan presentation is a cross-sectional view of structure 111. In a typical B-scan presentation, the travel time of a sound wave is displayed along a vertical axis and the linear position of the transducer is displayed along the horizontal axis. Thus, the depth of a reflecting surface can be illustrated in the B-scan presentation. The B-scan is typically produced by establishing a gray scale corresponding to the amplitude of each point on the A-scan waveform. Whenever the intensity of the signal is high, pixels of corresponding intensity are produced on the B-scan. Peaks in the A-scan waveform, for example, may appear to be light gray or white, while low level or baseline portions of the A-scan waveform are black. Processes for converting A-scan data to B-scan data are known to those skilled in the art of ultrasonic measurements.

According to the embodiments described herein, inspection device 100 is used to collect A-scan data while transducer assembly 101 is rotated within hole 114 of laminated structure 111. Thus, instead of collecting A-scan data at a single fixed location within hole 114, inspection device 100 collects A-scan data for multiple angular positions within hole 114 as transducer assembly 101 is rotated. Inspection device 100 is then able to plot the A-scan data for the different angular positions into a B-scan presentation. Thus, inspection device 100 can show a 360 degree image of the anomalies detected proximate to hole 114 over the span of the transducer beam width. An exemplary process for inspecting hole 114 with inspection device 100 is further described in FIG. 6.

Figure 6:
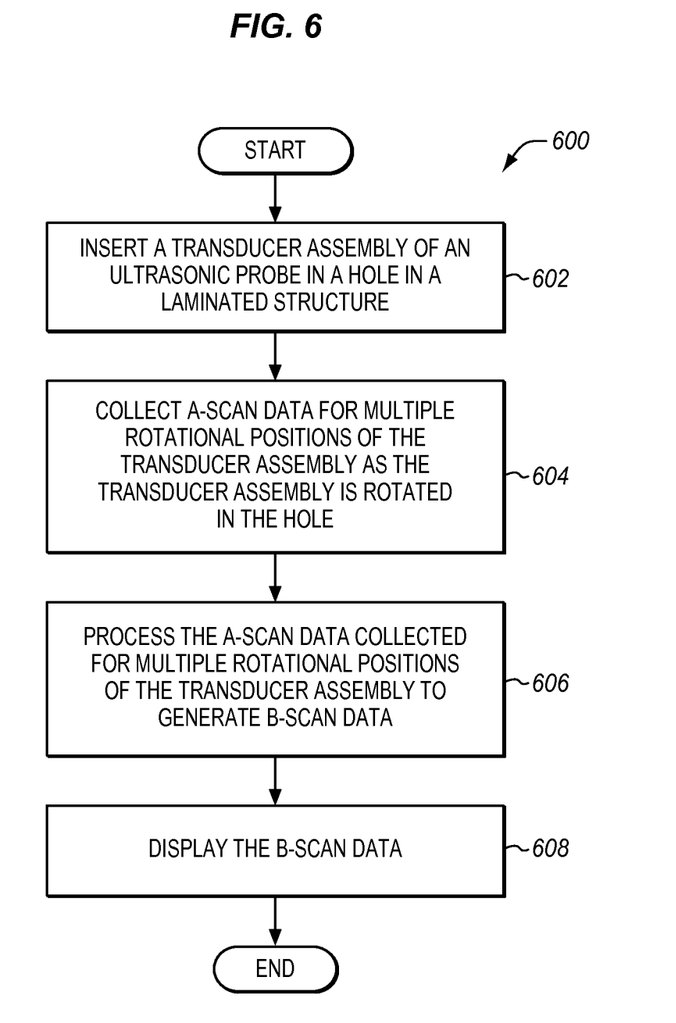
FIG. 6 is a flow chart illustrating a method for inspecting a hole in a laminated structure in an exemplary embodiment.

FIG. 6 is a flow chart illustrating a method 600 for inspecting the hole 114 in laminated structure 111 in an exemplary embodiment. The steps of method 600 will be described with reference to inspection device 100 in FIG. 1, but those skilled in the art will appreciate that method 600 may be performed in other systems. Also, the steps of the flow charts described herein are not all inclusive and may include other steps not shown, and the steps may be performed in an alternative order.

To start the inspection process, ultrasonic probe 101 is inserted in the hole 114 in laminated structure 111 in step 602. When ultrasonic probe 101 is inserted in the hole 114, the transducer assembly 208 is likewise inserted in the hole 114 and in a position to inspect the condition of hole 114. FIG. 4 illustrates transducer assembly 208 inserted in hole 114. With transducer assembly 208 inserted in hole 114, controller 108 collects A-scan data for multiple rotational positions of transducer assembly 208 as transducer assembly 208 is rotated within the hole in step 604. As shown in FIG. 4, transducer assembly 208 is able to rotate within hole 114. As transducer assembly 208 rotates, the sound waves emitted from the side 320 of transducer rod 304 are launched into different locations around the circumference of hole 114. Controller 108 associates the A-scan data with rotational positions of transducer assembly 208. For example, each time A-scan data is collected at a rotational position of transducer assembly 208, controller 108 may create an association or a pointer between the A-scan data and the rotational position. By collecting A-scan data as transducer assembly 208 is rotated, controller 108 is able to collect A-scan data for a portion or the entire circumference of hole 114. If the depth of the hole 114 exceeds the width of the sound beam, then probe 101 is indexed downward by one sound beam increment and a second 360-degree rotational scan is performed.

Transducer assembly 208 may be continuously rotated while A-scan data is collected, or may be sequentially rotated by turning transducer assembly 208 a particular amount, then pausing transducer assembly 208 while A-scan data is collected at this position. Transducer assembly 208 may then be turned a particular amount, and then paused while A-scan data is collected at another position.

Figure 7:
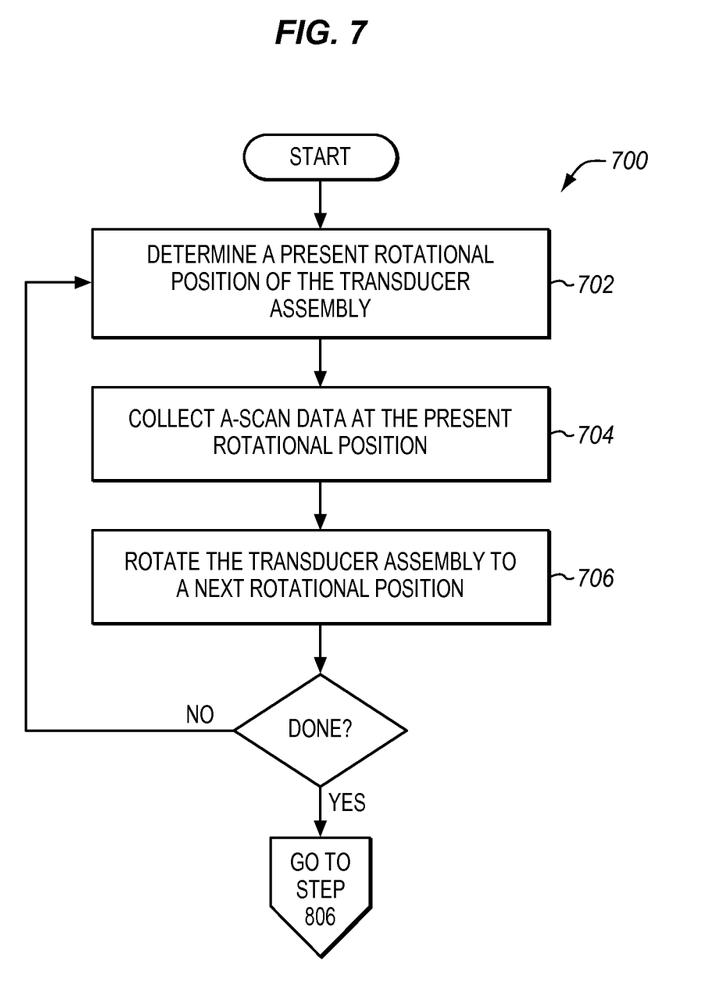
FIG. 7 is a flow chart illustrating a method for collecting A-scan data in an exemplary embodiment.

FIG. 7 is a flow chart illustrating a method 700 for collecting A-scan data in an exemplary embodiment. In step 702, controller 108 determines a present rotational position of transducer assembly 208 in hole 114. To determine the rotational position of transducer assembly 208 at any given time, controller 108 may receive position data from rotary encoder 218 that is in contact with transducer assembly 208. In step 704, controller 108 collects A-scan data at the present rotational position. The A-scan data collected is therefore associated with the present rotational position of transducer assembly 208. In step 706, transducer assembly 208 is rotated in hole 114 to a next rotational position. Transducer assembly 208 may be manually rotated, or may be rotated with an actuator system that is controlled by controller 108. Steps 702-706 then repeat until A-scan data is collected for the desired inspection area of hole 114. For example, an operator may want to inspect the entire 360 degree circumference of hole 114, so steps 702-706 may repeat for a full rotation of transducer assembly 208 within hole 114. If an operator wants to inspect a portion of the circumference of hole 114, then steps 702-706 may repeat for a quarter rotation of transducer assembly 208, a half rotation of transducer assembly 208, etc.

Figure 8:
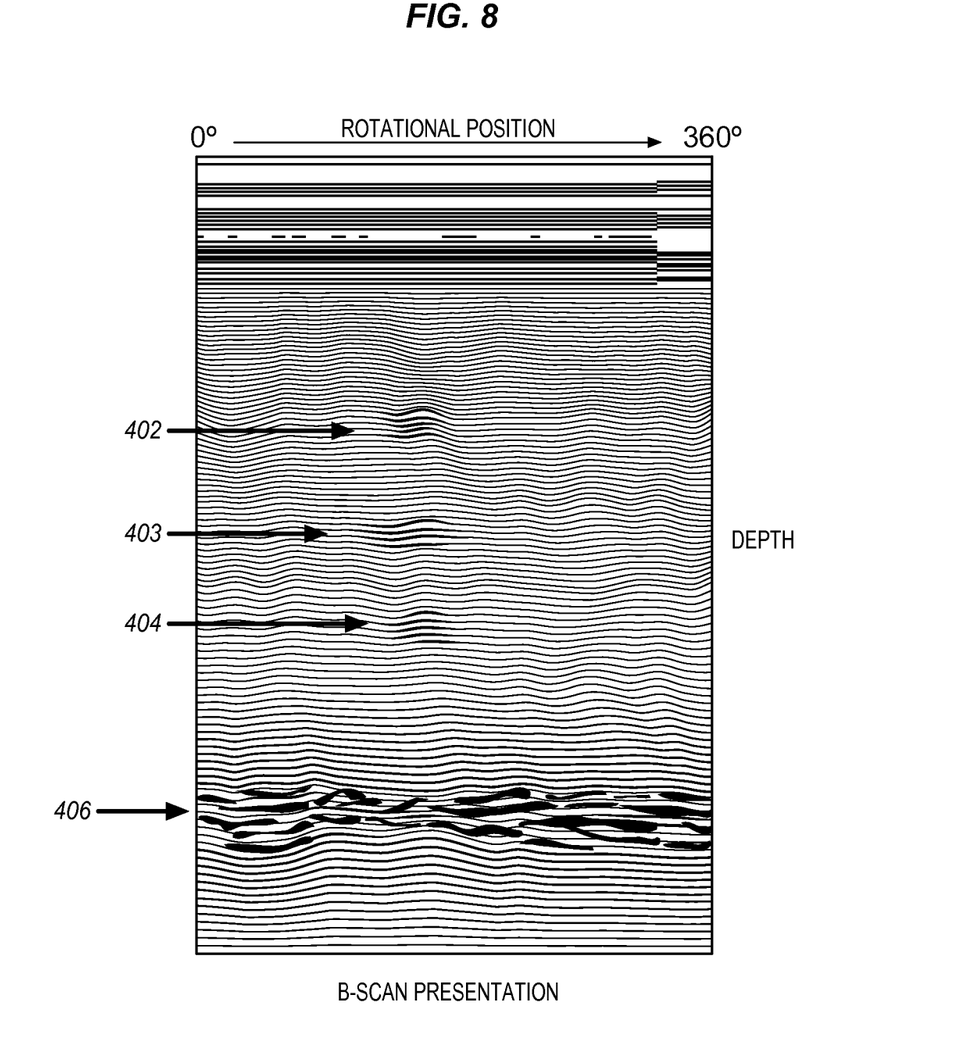
FIG. 8 illustrates B-scan data for a 360 degree rotation of a transducer assembly in an exemplary embodiment.

After A-scan data is collected for multiple rotational positions of transducer assembly 208, controller 108 processes the A-scan data for the multiple rotational positions of transducer assembly 208 to generate B-scan data (step 606). Controller 108 then displays the B-scan data in step 608 as a B-scan presentation. FIG. 8 illustrates B-scan data for a 360 degree rotation of transducer assembly 208 in an exemplary embodiment. The horizontal axis in FIG. 8 illustrates a 360 degree rotation of transducer assembly 208. The vertical axis in FIG. 8 illustrates a depth of reflective surfaces within laminated structure 111 (based on the travel time of echo waves reflecting off the reflective surfaces from various points within the sound beam). When the A-scan data for multiple rotational positions of transducer assembly 208 is compiled as B-scan data, a presentation of the B-scan data shows the surface of laminated structure 111, the depth of anomalies 402-404 within laminated structure 111, and where the anomalies 402-404 are located along the circumference of hole 114. For example, FIG. 8 shows that the anomalies 402-404 were detected when transducer assembly 208 was between about 100-200 degrees of its rotation. Therefore, an operator can more effectively identify where anomalies 402-404 appear in hole 114 of laminated structure 111 and their depth below the surface 406.

After performing measurements for a 360 degree rotation of transducer assembly 208, the depth of transducer assembly 208 may be changed in the hole 114. For example, an operator may turn depth index wheel 216 (see FIG. 2) in one direction or another to push transducer assembly 208 deeper into hole 114 or to pull transducer assembly 208 out of hole 114. The depth of transducer assembly 208 may be incrementally changed by an amount corresponding with a width of the sound beam produced by transducer assembly 208. After transducer assembly 208 is set at the new depth, controller 108 may collect A-scan data for multiple rotational positions of transducer assembly 208 as transducer assembly 208 is rotated within the hole 114 at the new depth. This process may continue at multiple depths.

Any of the various elements shown in the figures or described herein may be implemented as hardware, software, firmware, or some combination of these. For example, an element may be implemented as dedicated hardware. Dedicated hardware elements may be referred to as "processors", "controllers", or some similar terminology. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, a network processor, application specific integrated circuit (ASIC) or other circuitry, field programmable gate array (FPGA), read only memory (ROM) for storing software, random access memory (RAM), non-volatile storage, logic, or some other physical hardware component or module.

Also, an element may be implemented as instructions executable by a processor or a computer to perform the functions of the element. Some examples of instructions are software, program code, and firmware. The instructions are operational when executed by the processor to direct the processor to perform the functions of the element. The instructions may be stored on storage devices that are readable by the processor. Some examples of the storage devices are digital or solid-state memories, magnetic storage media such as a magnetic disks and magnetic tapes, hard drives, or optically readable digital data storage media.

Although specific embodiments were described herein, the scope is not limited to those specific embodiments. Rather, the scope is defined by the following claims and any equivalents thereof.

The invention claimed is:

1. A method for inspecting a hole in a laminated structure using an ultrasonic inspection device, wherein the ultrasonic inspection device includes a transducer assembly configured to direct sound waves substantially parallel to a surface of the hole, the method comprising:
   inserting the transducer assembly in the hole in the laminated structure;
   collecting A-scan data for multiple rotational positions of the transducer assembly as the transducer assembly is rotated within the hole in the laminated structure, wherein collecting the A-scan data at one of the rotational positions comprises:
      generating an ultrasonic sound wave in a transducer of the transducer assembly that is directed toward a side of an elongated transducer rod, wherein the ultrasonic sound wave refracts, when passing through the side of the transducer rod due to a material used for the transducer rod, at an angle substantially parallel to the surface of the hole in the laminated structure;

receiving at least one echo wave at the transducer; and converting the at least one echo wave into the A-scan data;

processing the A-scan data for the multiple rotational positions of the transducer assembly in the hole in the laminated structure to generate B-scan data; and displaying the B-scan data to illustrate a depth of an anomaly within the laminated structure, and to illustrate where the anomaly is located along a circumference of the hole in the laminated structure.

2. The method of claim 1 wherein collecting A-scan data for multiple rotational positions of the transducer assembly comprises:

associating the A-scan data with each of the multiple rotational positions of the transducer assembly.

3. The method of claim 1 wherein collecting A-scan data for multiple rotational positions of the transducer assembly comprises:

repeatedly performing the steps of:
determining a present rotational position of the transducer assembly in the hole;
collecting the A-scan data at the present rotational position; and
rotating the transducer assembly in the hole to a next rotational position.

4. The method of claim 3 wherein determining a present rotational position of the transducer assembly comprises:

receiving position data from a rotary encoder coupled to the transducer rod.

5. The method of claim 1 wherein:

the ultrasonic sound wave comprises an ultrasonic subsurface longitudinal wave (SSL-wave) that propagates through the laminated structure substantially parallel to the surface of the hole in the laminated structure.

6. The method of claim 1 wherein collecting A-scan data for multiple rotational positions of the transducer assembly comprises:

collecting the A-scan data for the multiple rotational positions of a 360 degree rotation of the transducer assembly within the hole.

7. The method of claim 6 further comprising:

changing a depth of the transducer assembly in the hole by an amount corresponding with a width of the ultrasonic sound wave; and repeating the collection of the A-scan data for the multiple rotational positions of a 360 degree rotation of the transducer assembly within the hole at the new depth.

8. An ultrasonic inspection device for inspecting a hole in a laminated structure, the ultrasonic inspection device comprising:

an ultrasonic probe that includes a transducer assembly for insertion into the hole in the laminated structure; and a controller coupled to the transducer assembly;

the transducer assembly includes a transducer configured to generate an ultrasonic sound wave, and includes an elongated transducer rod;

the transducer is mounted on an end of the transducer rod and is angled toward a side of the transducer rod to direct the ultrasonic sound wave toward the side of an elongated transducer rod, wherein the ultrasonic sound wave refracts, when passing through the side of the transducer rod due to a material used for the transducer rod, at an angle substantially parallel to a surface of the hole in the laminated structure;

the transducer receives at least one echo wave, and converts the at least one echo wave into an electrical signal that is provided to the controller;

the controller is configured to collect A-scan data for multiple rotational positions of the transducer assembly as the transducer assembly is rotated within the hole in the laminated structure based on the electrical signal from the transducer, to process the A-scan data for the multiple rotational positions of the transducer assembly in the hole in the laminated structure to generate B-scan data, and to display the B-scan data to illustrate a depth of an anomaly within the laminated structure and to illustrate where the anomaly is located along a circumference of the hole in the laminated structure.

9. The ultrasonic inspection device of claim 8 wherein:

the controller is further configured to associate the A-scan data with each of the multiple rotational positions of the transducer assembly.

10. The ultrasonic inspection device of claim 8 wherein:

the controller is configured to collect the A-scan data for the multiple rotational positions of the transducer assembly by repeatedly performing the steps of:
determining a present rotational position of the transducer assembly in the hole;
collecting the A-scan data at the present rotational position; and
rotating the transducer rod in the hole to a next rotational position.

11. The ultrasonic inspection device of claim 8 wherein:

the ultrasonic sound wave comprises an ultrasonic subsurface longitudinal wave (SSL-wave) that propagates through the laminated structure substantially parallel to the surface of the hole in the laminated structure.

12. The ultrasonic inspection device of claim 8 further comprising:

a rotary encoder configured to provide position data for the transducer assembly.

13. The ultrasonic inspection device of claim 8 wherein:

the controller is configured to collect the A-scan data for the multiple rotational positions of a 360 degree rotation of the transducer assembly within the hole.

14. The ultrasonic inspection device of claim 8 wherein:

the transducer assembly includes a depth mechanism that changes a depth of the transducer assembly in the hole by an amount corresponding with a width of the ultrasonic sound wave; and the controller is configured to repeat the collection of the A-scan data for the multiple rotational positions of a 360 degree rotation of the transducer assembly within the hole at the new depth.

15. A method for inspecting a hole in a laminated structure, the method comprising:

inserting a transducer assembly of an ultrasonic probe into a hole in a laminated structure;

collecting A-scan data for multiple rotational positions of the transducer assembly as the transducer assembly is rotated within the hole by:
determining a present rotational position of the transducer assembly;
generating an ultrasonic sound wave in a transducer of the transducer assembly that is directed toward a side of an elongated transducer rod, wherein the ultrasonic sound wave refracts, when passing through the side of the transducer rod due to a material used for the transducer rod, at an angle substantially parallel to a surface of the hole in the laminated structure;

receiving at least one echo wave at the transducer; and converting the at least one echo wave into the A-scan data that is associated with the present rotational position of the transducer assembly;

processing the A-scan data for the multiple rotational positions of the transducer assembly in the hole in the laminated structure to generate B-scan data; and displaying the B-scan data to illustrate a depth of an anomaly within the laminated structure, and to illustrate where the anomaly is located along a circumference of the hole in the laminated structure.

16. The method of claim 15 wherein determining a present rotational position of the transducer assembly comprises:

receiving position data from a rotary encoder.

17. The method of claim 15 further comprising:

sequentially rotating the transducer rod between different rotational positions.

18. The method of claim 15 wherein collecting A-scan data for multiple rotational positions of the transducer assembly comprises:

collecting the A-scan data for the multiple rotational positions of a 360 degree rotation of the transducer assembly within the hole.

19. The method of claim 18 further comprising:

changing a depth of the transducer assembly in the hole by an amount corresponding with a width of the ultrasonic sound wave; and repeating the collection of the A-scan data for the multiple rotational positions of a 360 degree rotation of the transducer assembly within the hole at the new depth.

* * * * *